(12) United States Patent
Hyeon et al.

(10) Patent No.: US 9,352,058 B2
(45) Date of Patent: May 31, 2016

(54) METHOD OF PREPARING IRON OXIDE NANOPARTICLES COATED WITH HYDROPHILIC MATERIAL, AND MAGNETIC RESONANCE IMAGING CONTRAST AGENT USING THE SAME

(75) Inventors: Taeghwan Hyeon, Seoul (KR); Yuanzhe Piao, Suwon-si (KR); Yong Il Park, Seoul (KR)

(73) Assignee: HANWHA CHEMICAL CORPORATION (KR)

( * ) Notice: Subject to any disclaimer, the term of this patent is extended or adjusted under 35 U.S.C. 154(b) by 0 days.

(21) Appl. No.: 13/983,367

(22) PCT Filed: Feb. 6, 2012

(86) PCT No.: PCT/KR2012/000845
§ 371 (c)(1),
(2), (4) Date: Aug. 23, 2013

(87) PCT Pub. No.: WO2012/108648
PCT Pub. Date: Aug. 16, 2012

(65) Prior Publication Data
US 2013/0323182 A1   Dec. 5, 2013

(30) Foreign Application Priority Data
Feb. 9, 2011  (KR) .................. 10-2011-0011294

(51) Int. Cl.
*A61B 5/055*   (2006.01)
*B05D 3/00*   (2006.01)
(Continued)

(52) U.S. Cl.
CPC .......... *A61K 49/1824* (2013.01); *A61K 49/186* (2013.01); *A61K 49/1863* (2013.01);
(Continued)

(58) Field of Classification Search
CPC ............ A61K 49/186; A61K 49/1863; A61K 49/1824; C01G 49/02; C09C 1/24; C09C 3/08; B82Y 30/00; B82Y 5/00; C01P 2002/72; C01P 2004/04; C01P 2004/51; C01P 2004/64; C01P 2004/03; C01P 2006/42
USPC .............................. 424/9.322, 9.32; 427/2.11
See application file for complete search history.

(56) References Cited

U.S. PATENT DOCUMENTS

2009/0309597 A1* 12/2009 Horak et al. ................. 324/318
2012/0201760 A1* 8/2012 Tromsdorf .............. C07F 9/091
424/9.322
2013/0195767 A1* 8/2013 Weissleder et al. ........ 424/9.323

FOREIGN PATENT DOCUMENTS

JP   1991141119   6/1991
JP   2009114066   5/2009
(Continued)

OTHER PUBLICATIONS

Park et al., Transformation of hydrophobic iron oxide nanoparticles to hydrophilic and biocompatible maghemite nanocrystals for use as highly efficient MRI contrast agent, J. Mater. Chem. (2011) 21: 11472-11477, 6 pages.*
(Continued)

*Primary Examiner* — Brian-Yong Kwon
*Assistant Examiner* — Miriam A Levin
(74) *Attorney, Agent, or Firm* — Cantor Colburn LLP

(57) ABSTRACT

The present invention relates to a method of preparing biocompatible iron oxide nanoparticles by coating iron oxide nanoparticles having improved magnetism via annealing treatment using salt particles with a hydrophilic material and to a magnetic resonance imaging (MRI) contrast agent including the iron oxide nanoparticles prepared thereby. Among hydrophilic materials, carboxymethyl dextran (CM-dextran) is the most efficient in terms of stabilizing the annealed iron oxide nanoparticles and exhibiting contrast effects.

17 Claims, 18 Drawing Sheets

(51) Int. Cl.
- *A61K 49/18* (2006.01)
- *C01G 49/02* (2006.01)
- *C09C 1/24* (2006.01)
- *B82Y 30/00* (2011.01)
- *C09C 3/08* (2006.01)

(52) U.S. Cl.
CPC .............. *B82Y 30/00* (2013.01); *C01G 49/02* (2013.01); *C09C 1/24* (2013.01); *C01P 2002/72* (2013.01); *C01P 2004/03* (2013.01); *C01P 2004/04* (2013.01); *C01P 2004/51* (2013.01); *C01P 2004/64* (2013.01); *C01P 2006/42* (2013.01); *C09C 3/08* (2013.01)

(56) References Cited

FOREIGN PATENT DOCUMENTS

| | | |
|---|---|---|
| JP | 2009531296 | 9/2009 |
| JP | 2010502992 | 1/2010 |
| WO | 2007095871 | 8/2007 |
| WO | 2009014201 | 1/2009 |
| WO | 2010134087 | 11/2010 |

OTHER PUBLICATIONS

Documentation of Mar. 16, 2011 publication date on-line, attached as NPL document, [Retrieved from internet <URL: http://pubs.rsc.org/en/Content/ArticleLanding/2011/JM/c1jm10432b#!divAbstract >] [Downloaded Mar. 23, 2015], 1 page.*

Written Opinion of the International Searching Authority (Sep. 12, 2012), 5 pages.*

Benjamin R Jarrett et al., Size-controlled synthesis of dextran sulfate coated iron oxide nanoparticles for magnetic resonance imaging, Nanotechnology, 2007, pp. 1-7.

International Search Report—PCT/KR2012/000845 dated Sep. 12, 2012.

Jae-Hyun Lee et al., Artificially engineered magnetic nanoparticles for ultra-sensitive molecular imaging, Nature Medicine, 2007, pp. 95-99.

Jongnam Park et al., Ultra-large-scale syntheses of monodisperse nanocrystals, nature materials, 2004, pp. 891-895.

Chu W. Jung et al., Physical and Chemical Properties of Superparamagnetic Iron Oxide MR Contrast Agents: Ferumoxides, Ferumoxtran, Ferumoxsil, Magnetic Resonance Imaging, 1995, pp. 661-674.

Suelin Chen, Polymer-Coated Iron Oxide Nanoparticles for Medical Imaging, Massachusetts Institute of Technology, 2010, pp. 1-158.

Anastasia Delattre et al., Stable Colloidal Solutions of High-Temperature-Annealed L10 FePt Nanoparticles**, Small, 2010, pp. 932-936.

Daren Li et al., Hard magnetic FePt nanoparticles by salt-matrix annealing, Journal of Applied Physics, 2006.

Yuanzhe Piao et al., Wrap-bake-peel process for nanostructural transformation from beta-FeOOH nanorods to biocompatible iron oxide nanocapsules, nauture materials, 2008, pp. 242-247.

* cited by examiner 69.2 ± 17.0 nm

METHOD OF PREPARING IRON OXIDE NANOPARTICLES COATED WITH HYDROPHILIC MATERIAL, AND MAGNETIC RESONANCE IMAGING CONTRAST AGENT USING THE SAME

TECHNICAL FIELD

The present invention relates to a method of preparing iron oxide nanoparticles coated with a hydrophilic material, wherein monodispersed iron oxide nanoparticles coated with an organic material are hydrophilized, and to a magnetic resonance imaging contrast agent including such nanoparticles. More particularly, the present invention relates to a method of preparing iron oxide nanoparticles coated with a hydrophilic material, comprising attaching iron oxide nanoparticles coated with an organic material onto salt particles, annealing them at high temperature to remove the organic material from the surface of the nanoparticles, and mixing the nanoparticles with an aqueous solution of hydrophilic material, thus obtaining iron oxide nanoparticles whose surface has been coated with the hydrophilic material, and to a contrast agent including the nanoparticles thus formed.

BACKGROUND ART

Magnetic nanoparticles have been widely used in such areas of the biomedical field as cell labeling, magnetic resonance imaging (MRI), drug delivery, and hyperthermia. Among a variety of kinds of magnetic nanoparticles, superparamagnetic iron oxide based nanoparticles have been broadly studied as a T2 MRI contrast agent because they have high magnetic susceptibility and superparamagnetic properties. T2 MRI contrast agents which are presently commercially available, such as Feridex, Resovist, and Combidex, are manufactured using reduction of iron chloride and co-precipitation in a hydrophilic polymer aqueous solution (C. W. Jung, et. al. Magn. Reson. Imaging 1995, 13, 661).

However, iron oxide nanoparticles thus manufactured have some defects. Because they are synthesized in an aqueous solution, it is difficult to perform a high-temperature reaction of 100° C. or more, and magnetism is lowered due to low crystallinity. Recently, to overcome such defects as these, thorough research is ongoing into how to improve the magnetism of materials and develop new T2 MRI contrast agents. Methods of synthesizing iron oxide nanoparticles having uniformity and high crystallinity were developed over the past ten years and mass production thereof has become possible (J. Park, et. al. Nat. Mater. 2004, 3, 891). For example, it is reported that manganese ferrite ($MnFe_2O_4$) nanoparticles have very high magnetism and thus exhibit superior T2 contrast effects (J.-H. Lee, et al. Nat. Med. 2007, 13, 95).

Unlike commercially available T2 MRI contrast agents, however, magnetic nanoparticles synthesized at a high temperature of 100° C. or more are not dispersed in an aqueous solution because they are coated with a hydrophobic surfactant. For biomedical applications, such hydrophobic magnetic nanoparticles should be coated with a biocompatible and hydrophilic material such as dextran, starch, polyethyleneglycol (PEG) or silica. Currently, dextran-coated iron oxide nanoparticles are medically approved as a T2 MRI contrast agent and are being used. However, because hydrophilic dextran is dispersed only in an aqueous solution, it is difficult to directly coat hydrophobic surfactant-coated nanoparticles. Thus, many attempts have been made to carry out additional modification so that hydrophilic dextran is dispersed in an organic solvent, or to disperse the nanoparticles in an aqueous solution before coating with dextran, but such methods are complicated and the yield is low.

In order to modify the structure of the material or improve the properties to solve the aforementioned problems, annealing treatment has been utilized. However, in the case of nanoparticles, high-temperature annealing treatment causes the particles to agglomerate thus losing the inherent properties of nanoparticles. To prevent such side-effects, recently a wrap-bake-peel method has been devised (Y. Piao, et al. Nat. Mater. 2008, 7, 242), so that the nanoparticles are coated with silica to prevent the nanoparticles from agglomerating during the annealing treatment.

Another method of preventing the particles from agglomerating during the annealing treatment, in which salt particles are used, has been proposed. Platinum-iron (Pt—Fe) nanoparticles having a face centered tetragonal (FCT) structure are mixed with an excess of sodium chloride (NaCl) followed by carrying out high-temperature annealing treatment thus forming Pt—Fe nanoparticles having a face centered cubic (FCC) structure (D. Li, et al. J. Appl. Phys. 2006, 99, 08E911). High-temperature annealing treatment modifies the crystalline structure of particles and thereby magnetism is enhanced.

In recent methods, NaCl is removed after which nanoparticles are dispersed in an aqueous solution and then coated with cysteine thus obtaining a very stable aqueous solution of nanoparticles (A. Delattre, et al. Small 2010, 6, 932).

DISCLOSURE

Technical Problem

The present invention is intended to provide a novel hydrophilic material coating method via annealing treatment using salt particles in order to solve problematic conventional techniques related to directly coating the hydrophobic surfactant-coated nanoparticles with a hydrophilic material.

Specifically, an object of the present invention is to provide a method of preparing iron oxide nanoparticles having increased stability and biocompatibility wherein the magnetism of organic material-coated iron oxide nanoparticles is improved via annealing treatment (FIG. 1) and the annealed iron oxide nanoparticles are coated with a hydrophilic material.

Another object of the present invention is to provide iron oxide nanoparticles coated with a hydrophilic material having improved magnetism and biocompatibility.

A further object of the present invention is to provide a magnetic resonance imaging (MRI) contrast agent comprising the nanoparticles having improved magnetism and biocompatibility.

Technical Solution

Iron oxide nanoparticles may be prepared by reacting an iron complex comprising iron as a center atom and a $C_4$~$C_{25}$ organic acid group (carboxylate) attached thereto as a ligand; a $C_4$~$C_{25}$ fatty acid; and a $C_4$~$C_{25}$ aliphatic alcohol or $C_4$~$C_{25}$ aliphatic amine at 150~350° C.

The iron precursor usable upon preparing the iron oxide nanoparticles is preferably provided in the form of a $C_{10}$~$C_{22}$ fatty acid ligand being attached to an iron atom, and more preferable precursor is iron oleate.

Also usable upon preparing the iron oxide nanoparticles, the fatty acid and the aliphatic alcohol (or aliphatic amine) may preferably include a $C_{10}$~$C_{22}$ fatty acid and aliphatic alcohol (or aliphatic amine). More preferably the fatty acid and the aliphatic alcohol may include oleic acid and oleyl alcohol respectively, and in the case of the aliphatic amine, oleyl amine is usable.

Preparing the iron oxide nanoparticles may be achieved by heating the reaction materials, for example, the iron complex, the fatty acid and the aliphatic alcohol (or aliphatic amine) to 200~310° C. from room temperature at a heating rate of at least 5° C./min so that they react at 200~310° C. for 5~60 min. The size of the iron oxide nanoparticles thus prepared may be controlled by adjusting the molar ratio of added reaction materials, namely, $C_4$~$C_{25}$ fatty acid and $C_4$~$C_{25}$ aliphatic alcohol (or aliphatic amine).

In addition, preparing the iron oxide nanoparticles may include reacting an iron complex comprising an iron center atom and a $C_4$~$C_{25}$ organic acid group (carboxylate) ligand attached thereto with a $C_4$~$C_{25}$ fatty acid at 290~320° C. at a heating rate of 3~3.5° C./min. Alternatively, an iron complex comprising an iron center atom and a $C_4$~$C_{25}$ organic acid group (carboxylate) ligand attached thereto and a $C_4$~$C_{25}$ fatty acid may be primarily reacted at 265~275° C. and then secondarily reacted at 315~325° C. thus preparing iron oxide nanoparticles. The iron oxide nanoparticles thus prepared may have a diameter of 1~100 nm, and preferably 2~20 nm. The kind of hydrophobic organic material attached to the surface of the prepared iron oxide nanoparticles is not limited but may preferably include at least one selected from a $C_4$~$C_{25}$ fatty acid, a $C_4$~$C_{25}$ aliphatic alcohol and a $C_4$~$C_{25}$ aliphatic amine, and the fatty acid which is a hydrophobic organic material is preferably oleic acid.

The mixture of iron oxide nanoparticles thus prepared and salt particles is annealed under air conditions, and an excess of the salt may be removed there from using distilled water. As such, the temperature may be decreased to room temperature before removing the salt. The kind of the salt is not limited but may preferably include sodium sulfate ($Na_2SO_4$), sodium chloride (NaCl), potassium chloride (KCl), calcium chloride ($CaCl_2$), sodium bicarbonate ($NaHCO_3$), potassium bicarbonate ($KHCO_3$) and calcium bicarbonate ($Ca(HCO_3)_2$). The salt particles have an average diameter of 1~500 μm, and preferably 150 μm or less. The weight ratio of iron oxide nanoparticles to the salt may be adjusted considering the diameter of iron oxide nanoparticles and the salt particles but may be preferably in the range of 1:10~1:1000. The annealing treatment of the mixture comprising iron oxide nanoparticles and the salt is possible even under the flow of an inert gas such as nitrogen, argon or neon but is the most preferable in air. The annealing treatment in an inert gas atmosphere is problematic because the original shape and size of the nanoparticles are not well maintained, and the efficient removal of the hydrophobic organic material in the form of carbon dioxide from the surface of the nanoparticles is possible under air. The annealing treatment temperature and the application time of air conditions may be adjusted but are preferably set to 400~600° C. and 1~10 hr. The process of removing the salt is not limited but preferably includes centrifugation which may be conducted under various conditions, for example, at about 13,000 rpm for about 30 min.

After annealing treatment and removal of the salt, the iron oxide nanoparticles are dispersed in an aqueous solution which is possible because of the hydroxyl group on the surface thereof. As the pH of the aqueous solution increases, changes in the zeta potential of the iron oxide nanoparticles may be observed.

Also in order to prepare more stable and biocompatible iron oxide nanoparticles in an aqueous solution, a hydrophilic material is used as a surface coating material. Examples of the hydrophilic material may include a dextran derivative, poly-acrylic acid, starch, silica, polyethyleneglycol (PEG) and PEG-phosphate (PO-PEGs). In order to prevent the particles from agglomerating during removal of the salt, coating with a hydrophilic material and removal of salt particles are simultaneously carried out (FIG. 1). The powder mixture of annealed nanoparticles and the salt is added to an aqueous solution of hydrophilic material. While the salt is dissolved in the aqueous solution of hydrophilic material, the nanoparticles are coated with the hydrophilic material. The hydrophilic material-coated nanoparticles are collected via centrifugation, and removal of the salt and coating with the hydrophilic material are repeated several times. In order to ascertain the dextran derivative which is suitable for stabilizing the annealed nanoparticles among hydrophilic materials, a variety of commercially available dextran derivatives may be used to coat the particles. The iron oxide nanoparticles coated with hydrophilic material may be analyzed using transmission electron microscopy (TEM) and dynamic light scattering (DLS).

The colloidal stability of the iron oxide nanoparticles coated with hydrophilic material may be measured based on the pH, NaCl concentration, and heat resistance. For biomedical applications, the nanoparticles should be stable in the presence of a predetermined amount of NaCl at a predetermined pH. The heat resistance is determined by measuring the binding force between the surface of the nanoparticles and the coating material. The stability test may be observed from changes in size with DLS.

Furthermore, a cell toxicity test of the iron oxide nanoparticles coated with hydrophilic material may be carried out, and a MTT method using MDA-MB-231 as breast cancer cells may be applied.

Moreover, the applicability of the iron oxide nanoparticles coated with hydrophilic material as a magnetic resonance imaging (MRI) contrast agent may be confirmed via animal MRI testing.

Advantageous Effects

According to the present invention, high-temperature annealing treatment can increase the crystallinity of nanoparticles to enhance the magnetism of iron oxide nanoparticles. Also, the iron oxide nanoparticles are coated with a hydrophilic material so as to ensure high stability and biocompatibility, and among a variety of hydrophilic materials, negatively charged carboxymethyl dextran (CM-dextran) is very effective at coating the nanoparticles to stabilize them. Because of their improved magnetism and coating of one or more nanoparticles with a dextran shell in the coating process, the contrast effects of the CM-dextran-coated iron oxide nanoparticles are superior.

DESCRIPTION OF DRAWINGS

The above and other objects, features and advantages of the present invention will become apparent from the following description of preferred embodiments given in conjunction with the accompanying drawings, in which.

MODE FOR INVENTION

Hereinafter, a detailed description will be given of preferred embodiments of the present invention with reference to the appended drawings.

The following examples which are set forth to illustrate but are not to be construed as limiting the present invention may provide a better understanding of the present invention, and may be appropriately modified or varied by those skilled in the art within the scope of the present invention.

Thus, the invention is to cover all modifications, equivalents, and alternatives falling within the spirit and scope of the invention as defined by the appended claims.

Transmission electron microscopy (TEM) was conducted using Jeol EM-2010 microscope, and X-ray diffraction (XRD) was carried out using Rigaku D/Max-3C diffractometer. The hydrodynamic diameter and zeta potential were measured using a particle size analyzer (ELS-Z2, Otsuka), and the M-H curve was determined using a vibrating sample magnetometer (VSM, Quantum Design PPMS).

Preparation Example

Synthesis of Iron Oxide Nanoparticles

Iron oxide nanoparticles were synthesized from an iron oleate complex prepared in a 100 L pilot plant according to the method disclosed in J. Park et al. Nat. Mater. 2004, 4, 891. This iron oleate complex was obtained by reacting sodium oleate with ferric chloride hexahydrate ($FeCl_3 \cdot 6H_2O$). Specifically, 1.08 kg of ferric chloride hexahydrate and 3.65 kg of sodium oleate were mixed with a solvent mixture comprising 6 L of water, 8 L of ethanol and 14 L of hexane and reacted at about 60° C. for 1 hr with vigorous stirring. The transparent lower layer was removed from the separated two layers and the remaining brownish organic layer was mixed with water after which the water layer was removed again to remove the remaining aqueous salt. This water-washing process was repeated three times. The hexane solvent was evaporated from the purified complex solution, thus obtaining an iron oleate complex.

Figure 1:
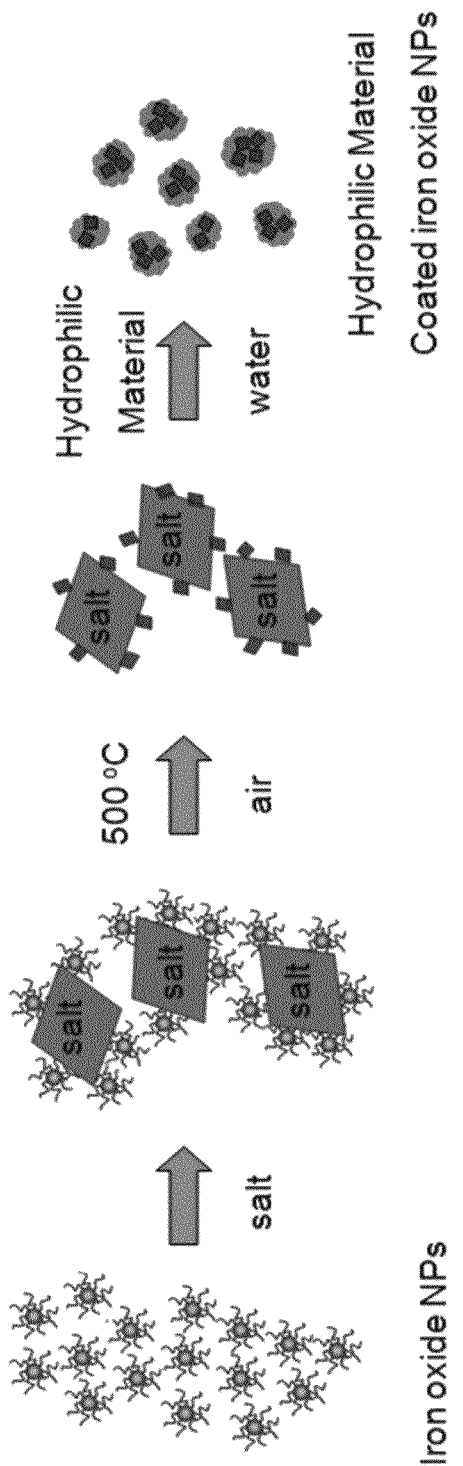
FIG. 1 shows a process comprising annealing iron oxide nanoparticles using salt particles and additionally coating them with a hydrophilic material.
Figure 2:
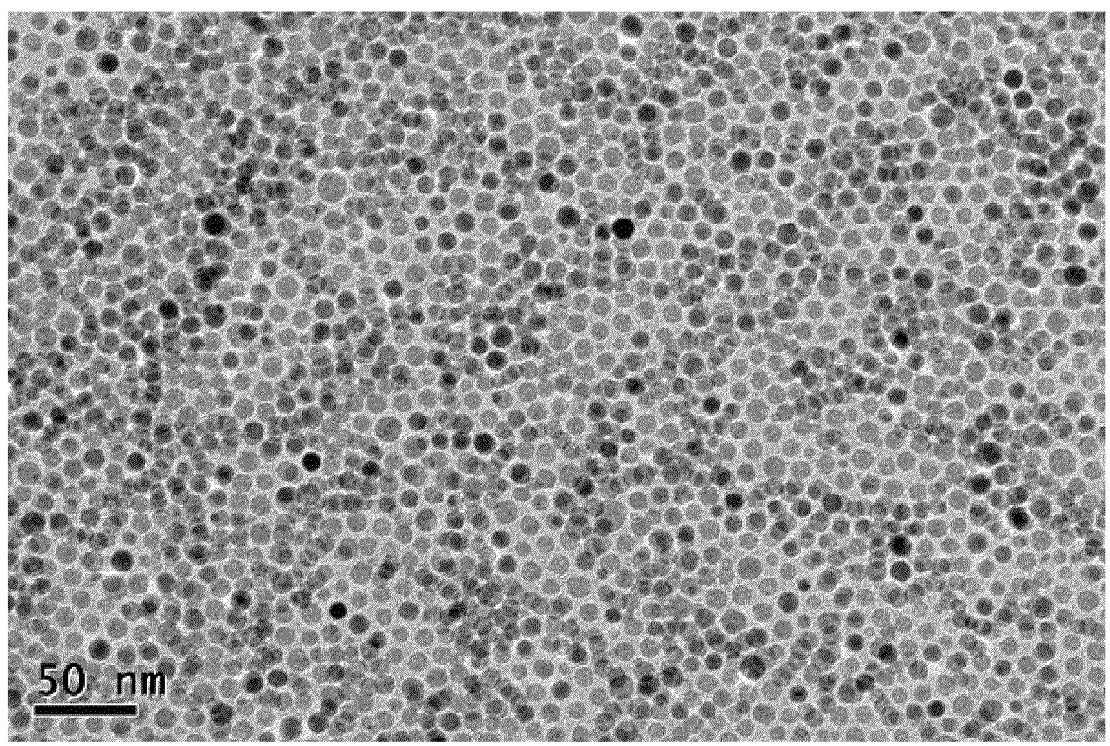
FIG. 2 shows a TEM image of 10 nm sized iron oxide nanoparticles.

3.6 kg (4 mol) of the iron oleate complex thus obtained and 0.57 kg (2 mol) of oleic acid were mixed with 20 kg of 1-octadecene, after which the resulting mixture was heated to 310° C. at a heating rate of 10° C./min so that it was allowed to react at 310° C. for 60 min, cooled to room temperature so that it was precipitated with a solution mixture having a 1:4 ratio of hexane to acetone, and then centrifuged, yielding iron oxide nanoparticles. Analysis using TEM of the synthesized iron oxide nanoparticles revealed a diameter of 10 nm (FIG. 2).

Example 1

Preparation of Iron Oxide Nanoparticles Having No Organic Material Via Annealing Treatment of Mixture Comprising Iron Oxide Nanoparticles and Salt Particles, and Measurement of Magnetism and Hydrodynamic Diameter of the Iron Oxide Nanoparticles Having No Organic Material 50 mg of the iron oxide nanoparticles thus synthesized and 25 g of sodium sulfate ($Na_2SO_4$) (average particle size of 150 μm) were stirred in hexane at a weight ratio of 1:500. While the temperature was increased, hexane was slowly evaporated. Thereafter, the powder mixture of nanoparticles and the salt was heated at 500° C. for 5 hr under air conditions. After annealing treatment, an excess of the salt was dissolved in distilled water and removed via centrifugation at 13,000 rpm for 30 min. In order to sufficiently remove the salt, washing using distilled water and centrifugation were repeated several times.

Figure 3:
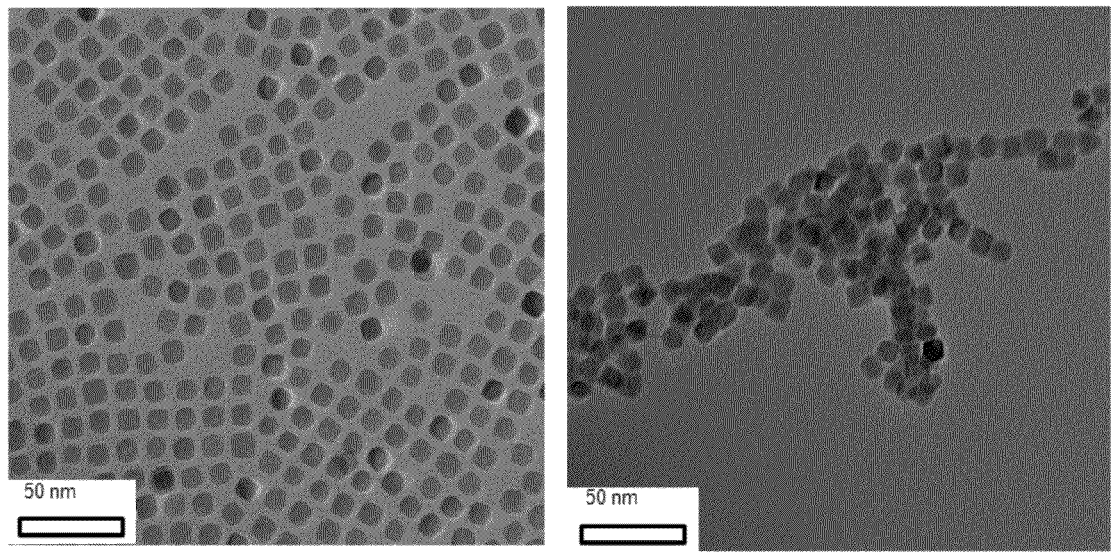
FIG. 3 shows TEM images of the iron oxide nanoparticles before and after annealing treatment wherein the left image shows the nanoparticles before annealing treatment and the right image shows the nanoparticles after annealing treatment.
Figure 4:
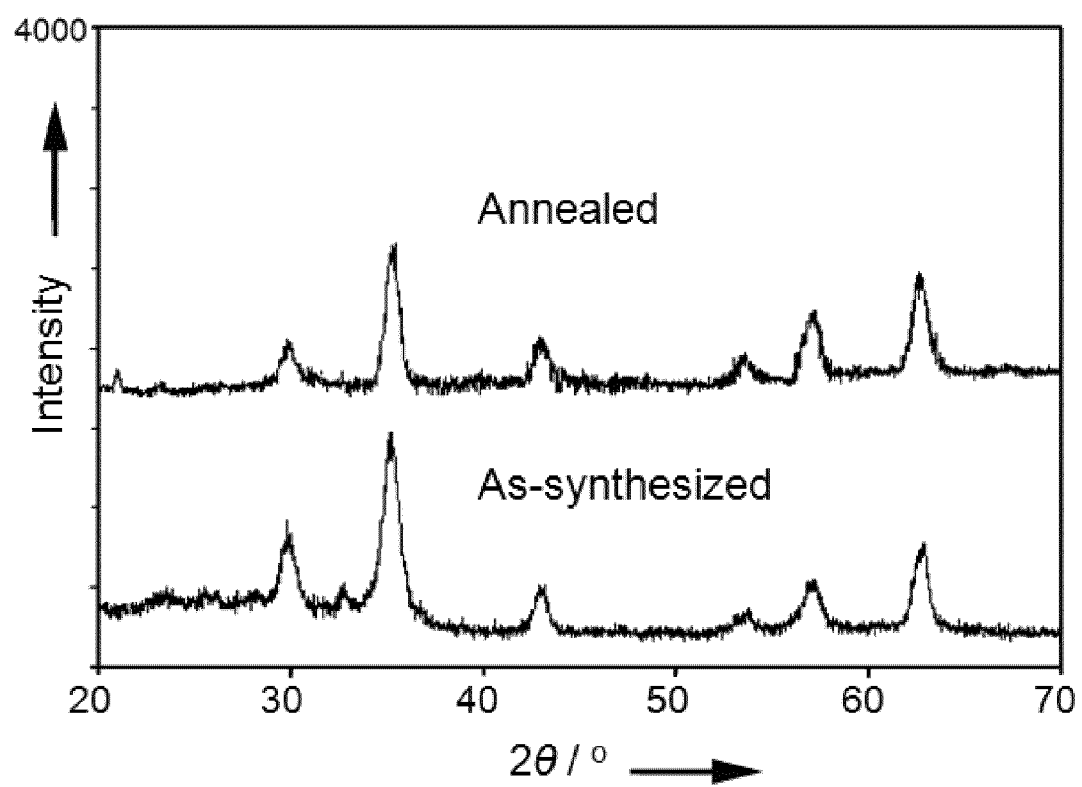
FIG. 4 shows X-ray diffraction (XRD) data of the iron oxide nanoparticles before and after annealing treatment.
Figure 5:
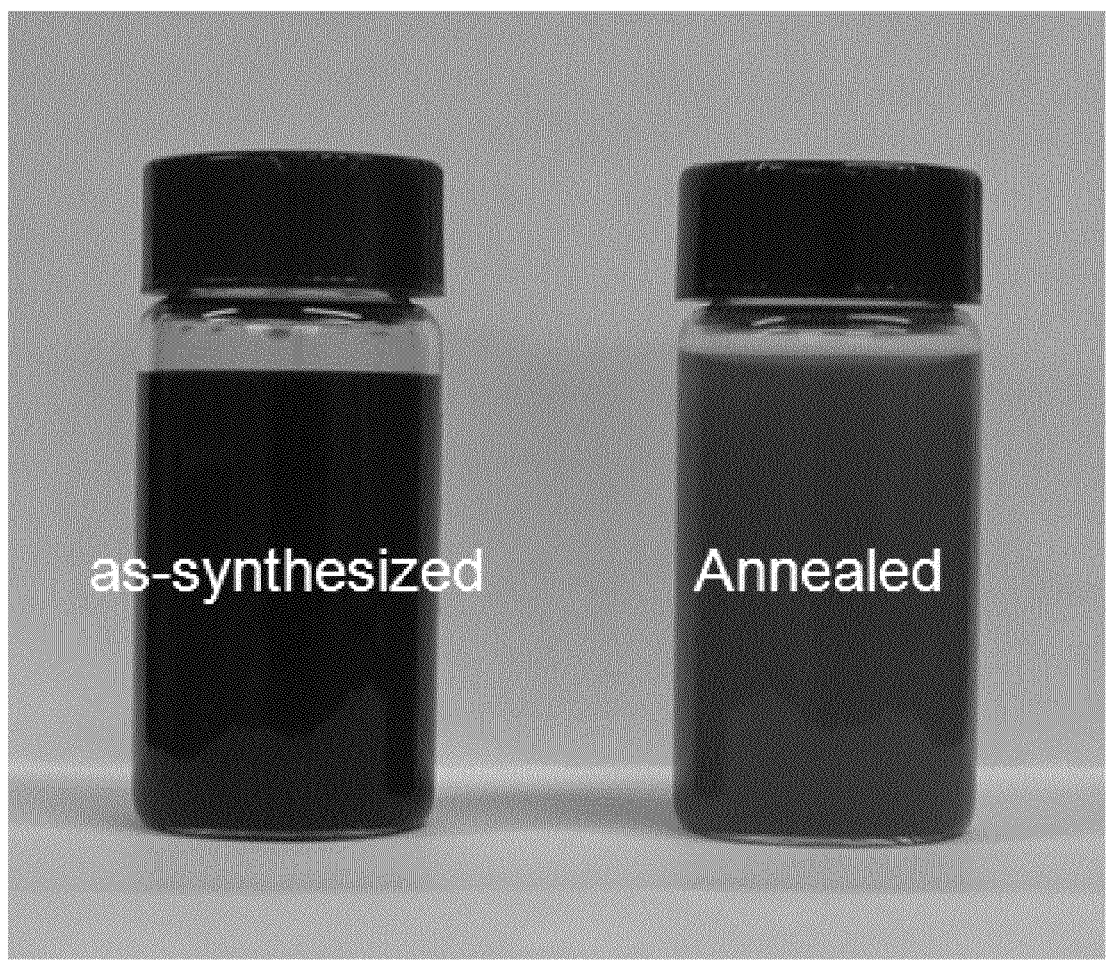
FIG. 5 shows the color of the iron oxide nanoparticles before and after annealing treatment.
Figure 6:
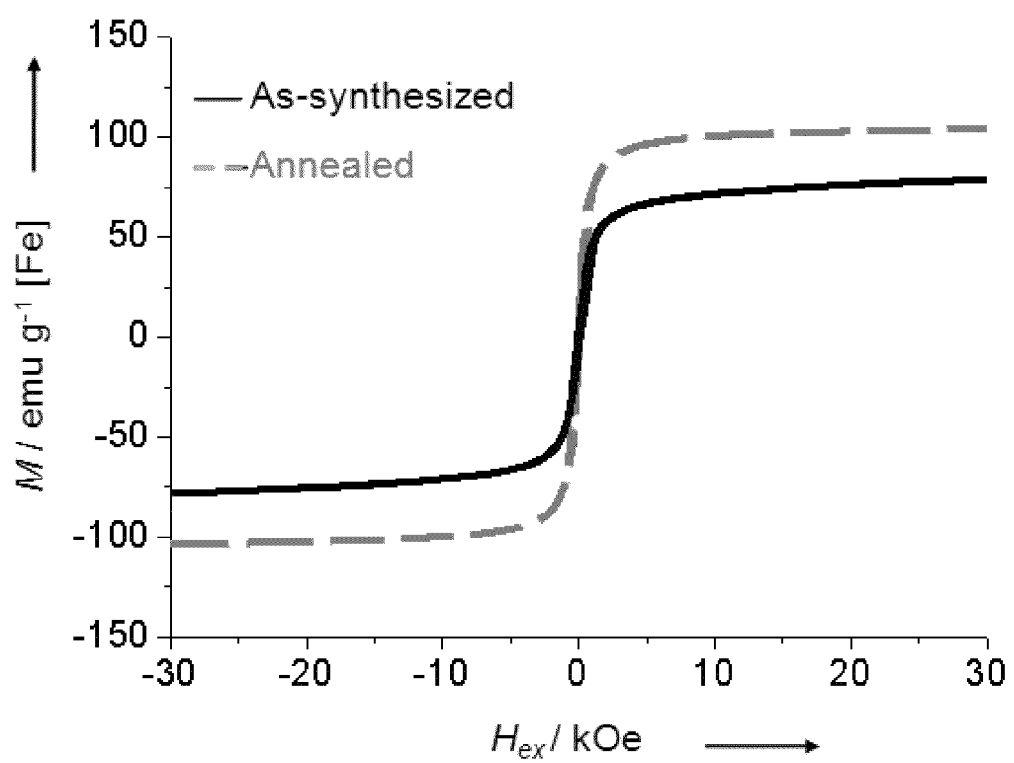
FIG. 6 is a graph showing the magnetic data of the iron oxide nanoparticles before and after annealing treatment.

Changes in physical properties of the iron oxide nanoparticles from which the organic material had been removed by annealing treatment using salt particles were analyzed. An increase in particle size due to the agglomeration of the particles during annealing treatment was not observed (FIG. 3). The crystalline structure of the annealed nanoparticles was analyzed via XRD (FIG. 4). The XRD pattern of the as-synthesized iron oxide nanoparticles was congruous with the XRD pattern of magnetite ($Fe_3O_4$, JCPDS 19-0629). As such, JCPDS (Joint Committee on Powder Diffraction Standards) is a file of diffraction data of materials collected and sorted from 1969 in which each of the diffraction patterns is recorded per card, and is thus used as a reference for determining the crystalline structure of a material from the measured XRD pattern. The XRD pattern of the nanoparticles after annealing treatment was similar to the XRD pattern of the nanoparticles before annealing treatment. Because small nanoparticles have a tendency to increase the width of the XRD peak, magnetite and maghemite ($\gamma$-$Fe_2O_3$, JCPDS 25-1402) having similar XRD patterns are difficult to clearly distinguish from each other via XRD analysis. Typically when magnetite is annealed under air conditions, it may become maghemite or hematite ($\alpha$-$Fe_2O_3$) via additional oxidation. However, the XRD pattern of hematite (JCPDS 24-0072) is apparently different from that of magnetite or maghemite. The iron oxide nanoparticles after annealing treatment are brownish, whereas the iron oxide nanoparticles before annealing treatment are black in color (FIG. 5). The annealed iron oxide nanoparticles appear to be maghemite via additional oxidation. In order to analyze changes in magnetism before and after annealing treatment, magnetism of the samples was measured using VSM. The saturation magnetization was 78 emu/g [Fe] before annealing treatment, and was 103 emu/g [Fe] after annealing treatment (FIG. 6). This is considered to be because crystallinity of the particles is increased via the high-temperature annealing treatment thus affecting the increase in magnetism.

The annealed iron oxide nanoparticles were dispersed in an aqueous solution to thus increase the pH of the aqueous solution, so that the zeta potential of the iron oxide nanoparticles was observed to change from a positive charge to a negative charge, and accordingly the hydrodynamic diameter was also changed (Table 1). At pH 7, the zeta potential of the annealed nanoparticles is small and the particles have a tendency to agglomerate and sink because of the absence of a surfactant for stabilizing the surface thereof. The hydrodynamic diameter of the nanoparticles measured at pH 7 was observed to exceed 1 µm, unlike under acidic or basic conditions (Table 1).

TABLE 1

| pH | Hydrodynamic Diameter (nm) | Zeta Potential (mV) |
| --- | --- | --- |
| 3 | 39.2 | 38.6 |
| 7 | 1555.9 | −10.73 |
| 10 | 76.5 | −34.99 |

Example 2

Preparation of Iron Oxide Nanoparticles Coated with Hydrophilic Material Via Annealing Treatment of Mixture Comprising Iron Oxide Nanoparticles and Salt Particles, and Measurement of Hydrodynamic Diameter and Stability of the Iron Oxide Nanoparticles Coated with Hydrophilic Material A mixture comprising iron oxide nanoparticles and salt particles was annealed in the same manner as in Example 1 with the exception that the iron oxide nanoparticles were coated with a hydrophilic material. Specifically, 1 g of a hydrophilic material (Table 2) was dissolved in 250 ml of distilled water. While the aqueous solution of hydrophilic material was stirred, 12.5 g of annealed iron oxide nanoparticles and the salt powder were slowly added at a weight ratio of 1:12.5. The iron oxide nanoparticles coated with hydrophilic material was separated via centrifugation at 13,000 rpm for 30 min. Additional washing using the aqueous solution of hydrophilic material and centrifugation were repeated two times more.

TABLE 2

| Kind | Molecular Weight |
| --- | --- |
| Carboxymethyl dextran sodium salt (CM-dextran) | ~12,000 |
| Dextran | ~1,500 |
| Diethyl aminoethyl-dextran hydrochloride (DEAE-dextran) | ~500,000 |
| Dextran sulfate sodium salt (DS) | ~4,000 |
| Polyacrylic acid | 1,800 |
| PEG | 2,805 |
| PO-PEGs | 2,000 (mPEG) |

Figure 7:
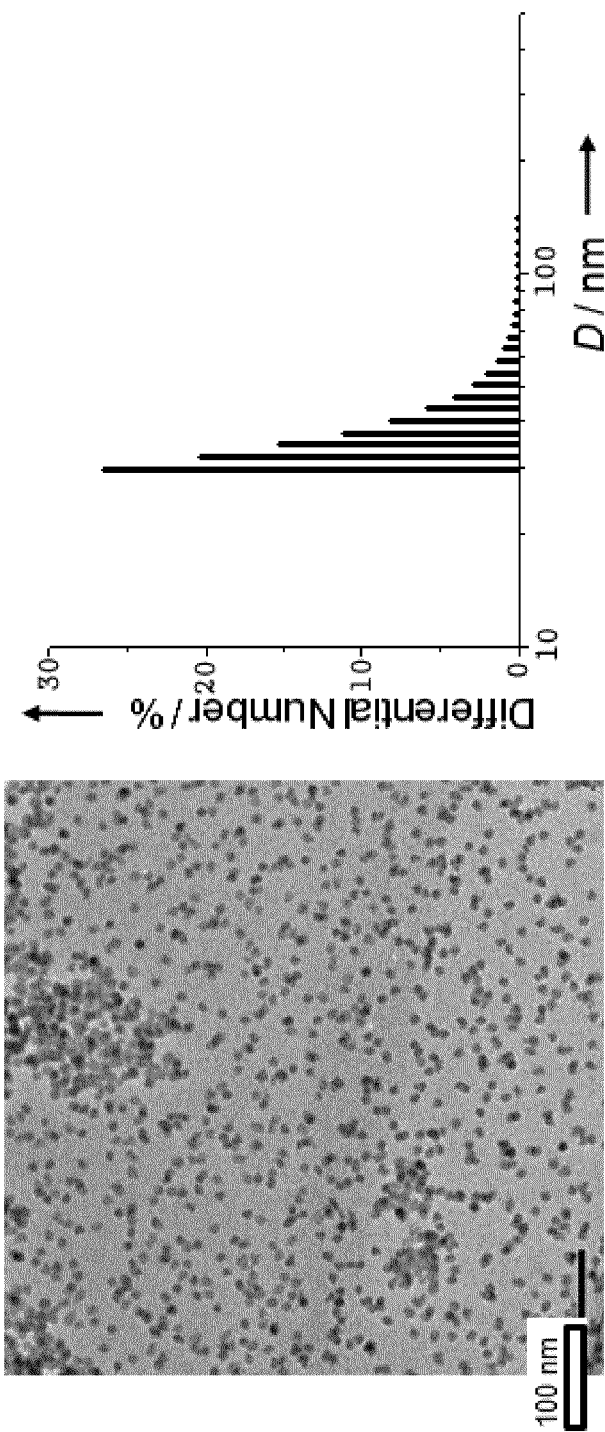
FIG. 7 shows a TEM image of dextran sulfate (DS)-coated iron oxide nanoparticles and a graph showing the hydrodynamic diameter thereof.
Figure 8:
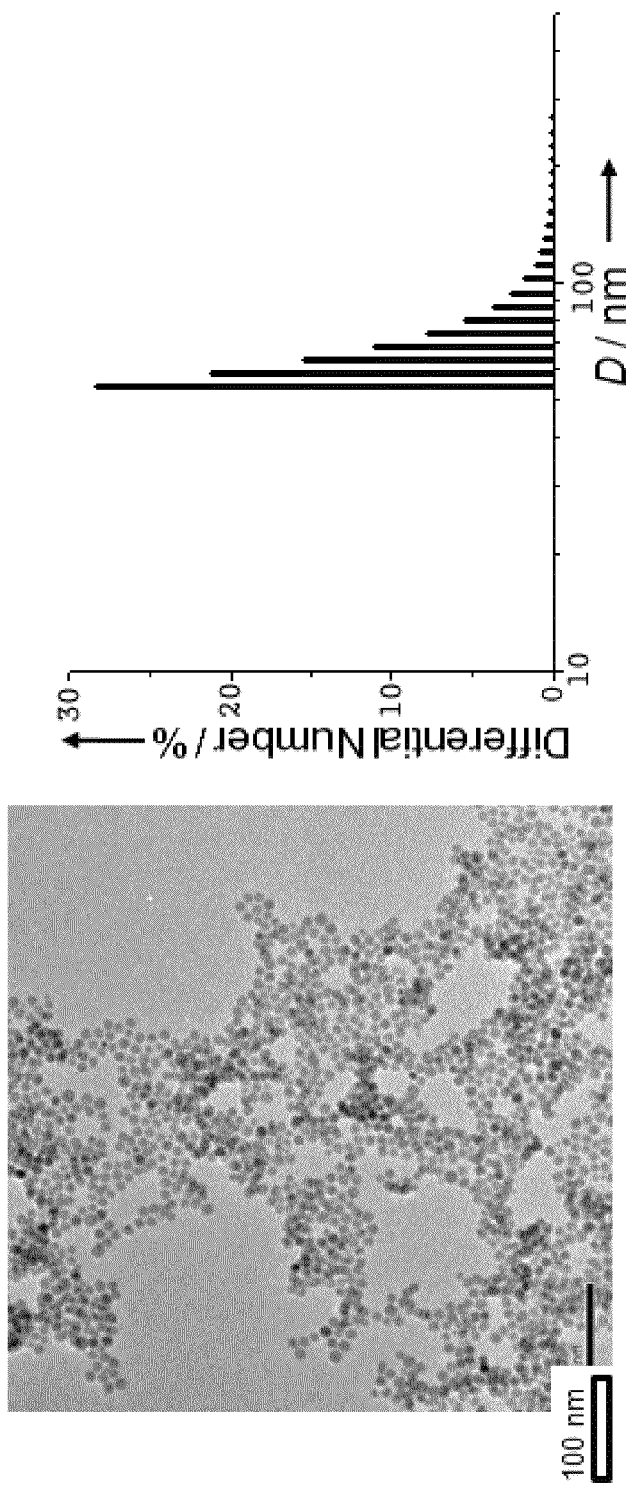
FIG. 8 shows a TEM image of CM-dextran-coated iron oxide nanoparticles and a graph showing the hydrodynamic diameter thereof.

In order to measure the shape and diameter of the iron oxide nanoparticles coated with hydrophilic material, TEM and DLS analysis were conducted. The iron oxide nanoparticles coated with positively charged DEAE-dextran were efficiently dispersed in the aqueous solution, and the hydrodynamic diameter thereof was 84.3 nm (Table 3). However, the coating efficiency of commercially available DEAE-dextran was low because of the large molecular weight. Among the negatively charged dextran derivatives, DS and CM-dextran were used for coating of the nanoparticles, and the coated iron oxide nanoparticles were stable in an aqueous solution for more than one month. The TEM images show no agglomeration of the particles in the course of coating with DS and CM-dextran (FIGS. 7 and 8). The hydrodynamic diameter of the DS-coated iron oxide nanoparticles was 36.8 nm (Table 3), which was similar to the value (28.7 nm) of the PEG-phospholipid-coated iron oxide nanoparticles (Table 3). However, the hydrodynamic diameter of the CM-dextran-coated iron oxide nanoparticles was 66.4 nm, which was much larger than that of the DS-coated or the PEG-phospholipid-coated iron oxide nanoparticles (Table 3). Hence, in the case of CM-dextran, one or more nanoparticles are considered to be coated together. For comparison, dextran having no charge was used for coating the nanoparticles. The hydrodynamic diameter of the coated particles exceeded 100 nm (Table 3), and such particles were observed to easily sink over time. From this, the electrostatic action between the nanoparticles and the coating material is regarded as affecting the coating efficiency of particles and the stability. Among a variety of kinds of dextran derivatives, negatively charged dextran was efficient at coating, and particularly the DS-coated nanoparticles represented the smallest hydrodynamic diameter.

Figure 9:
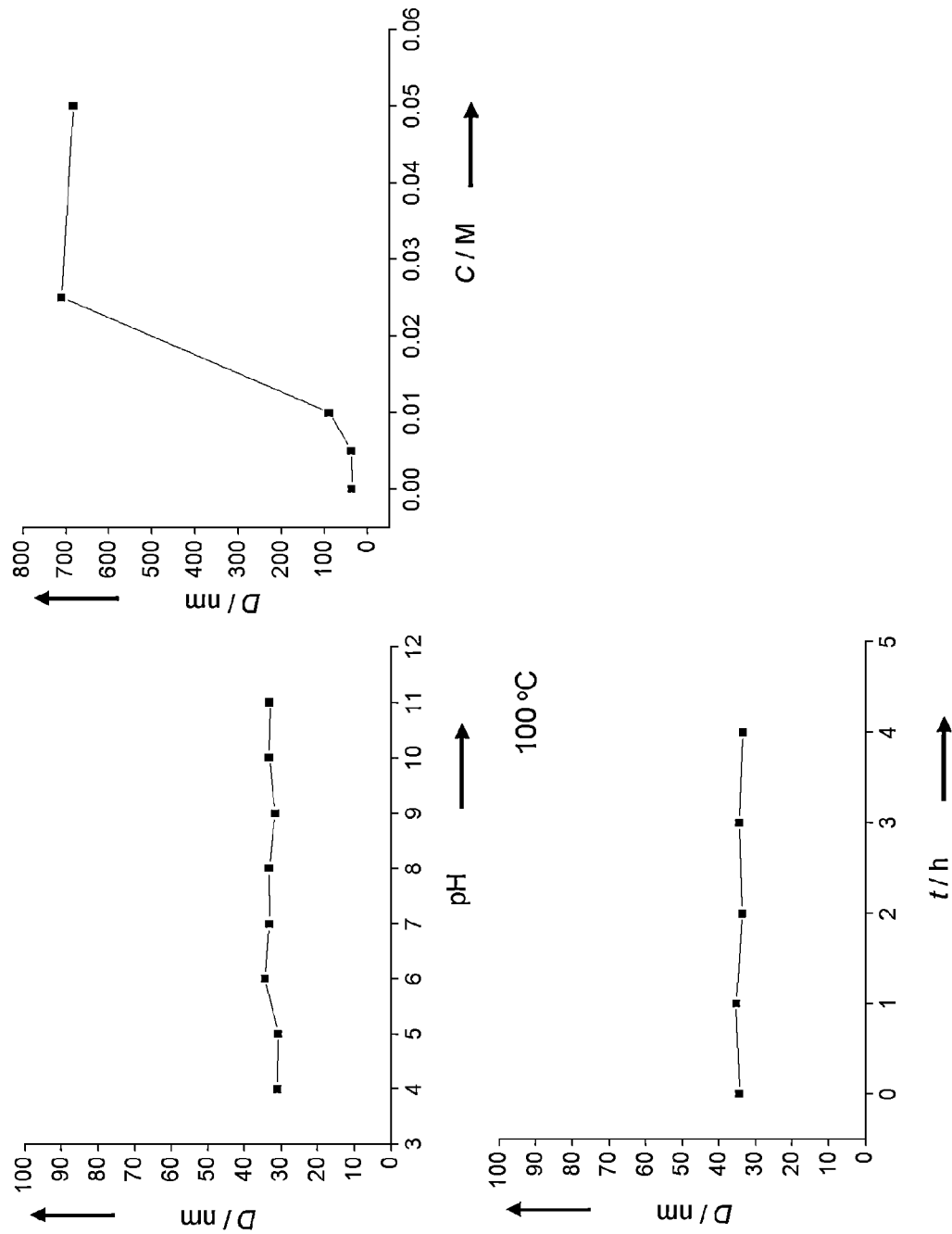
FIG. 9 is of graphs showing the stability test results of the DS-coated iron oxide nanoparticles.
Figure 10:
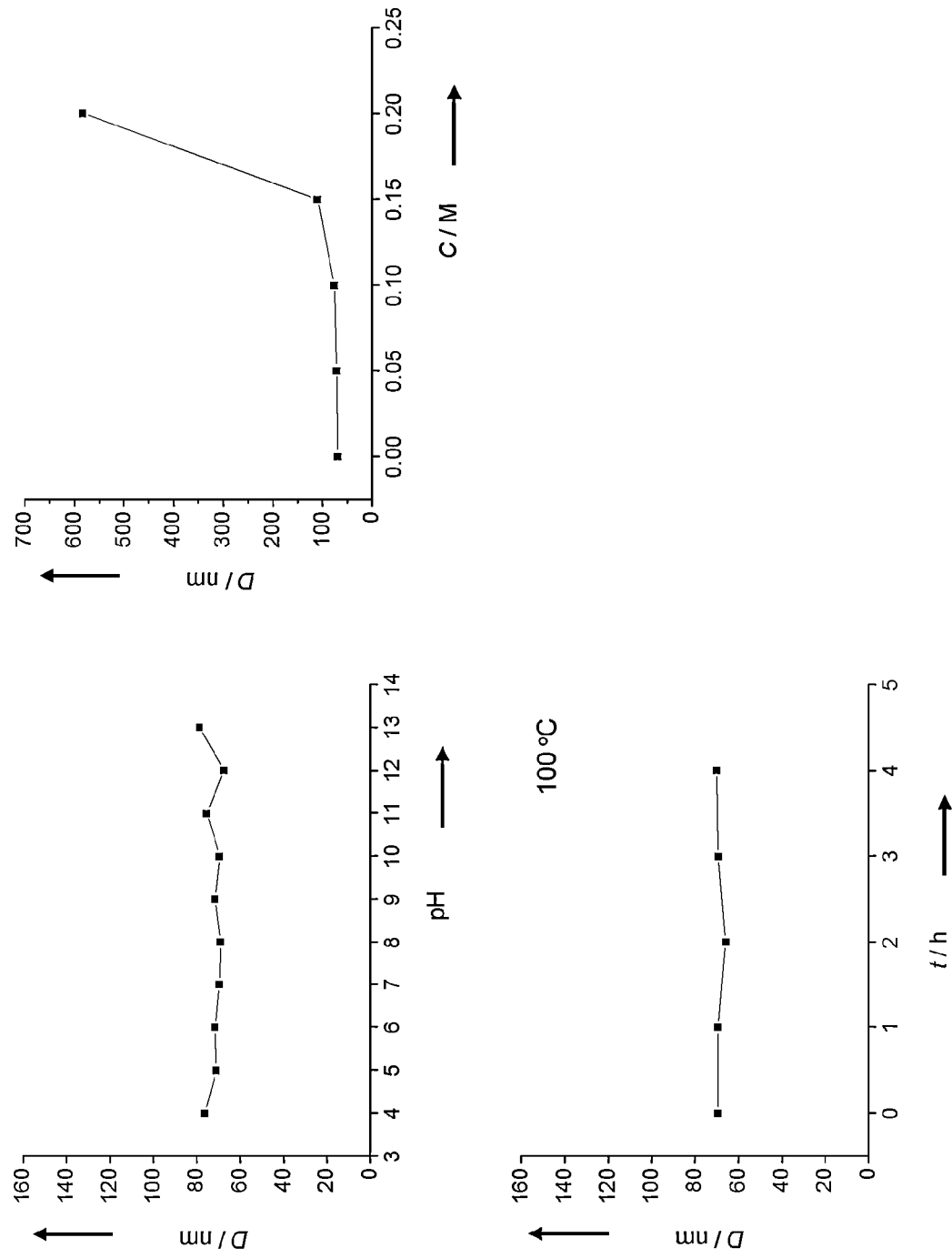
FIG. 10 is of graphs showing the stability test results of the CM-dextran-coated iron oxide nanoparticles.
Figure 11:
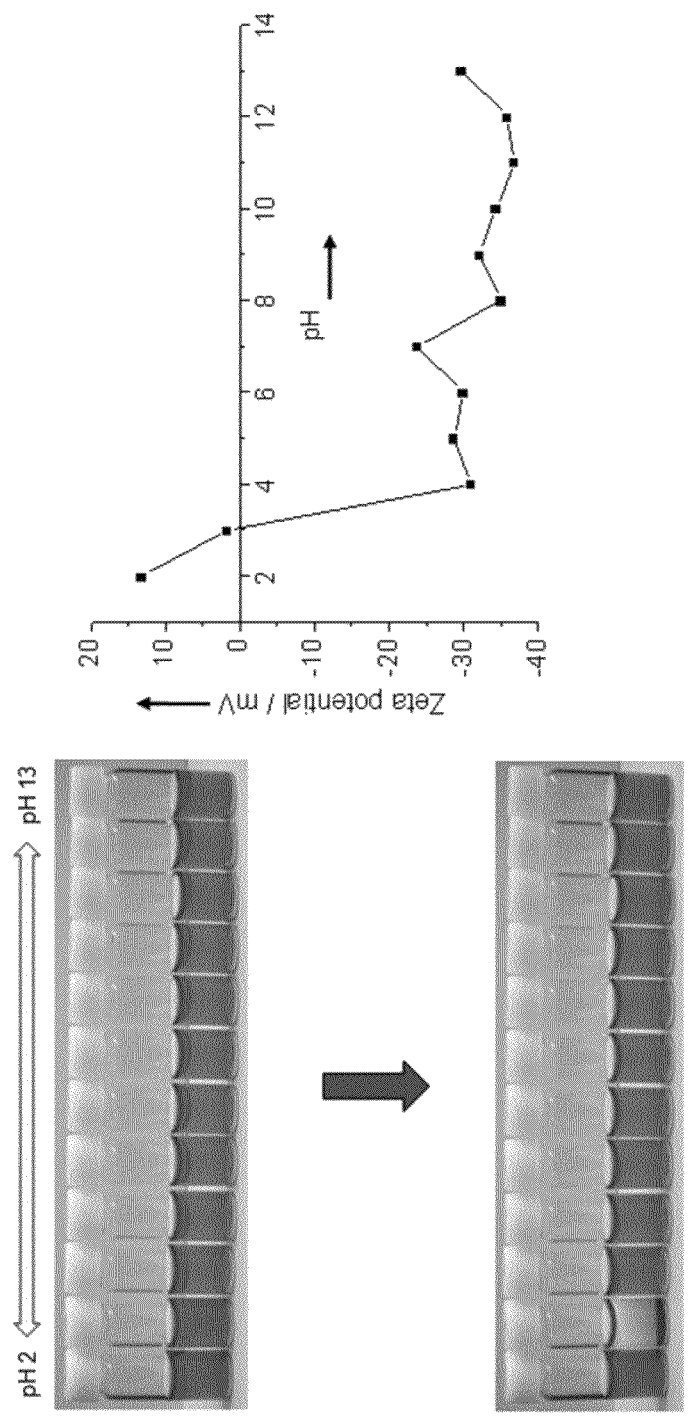
FIG. 11 shows photographs of samples of the CM-dextran-coated iron oxide nanoparticles with respect to changes in pH and a graph showing a zeta potential thereof.
Figure 12:
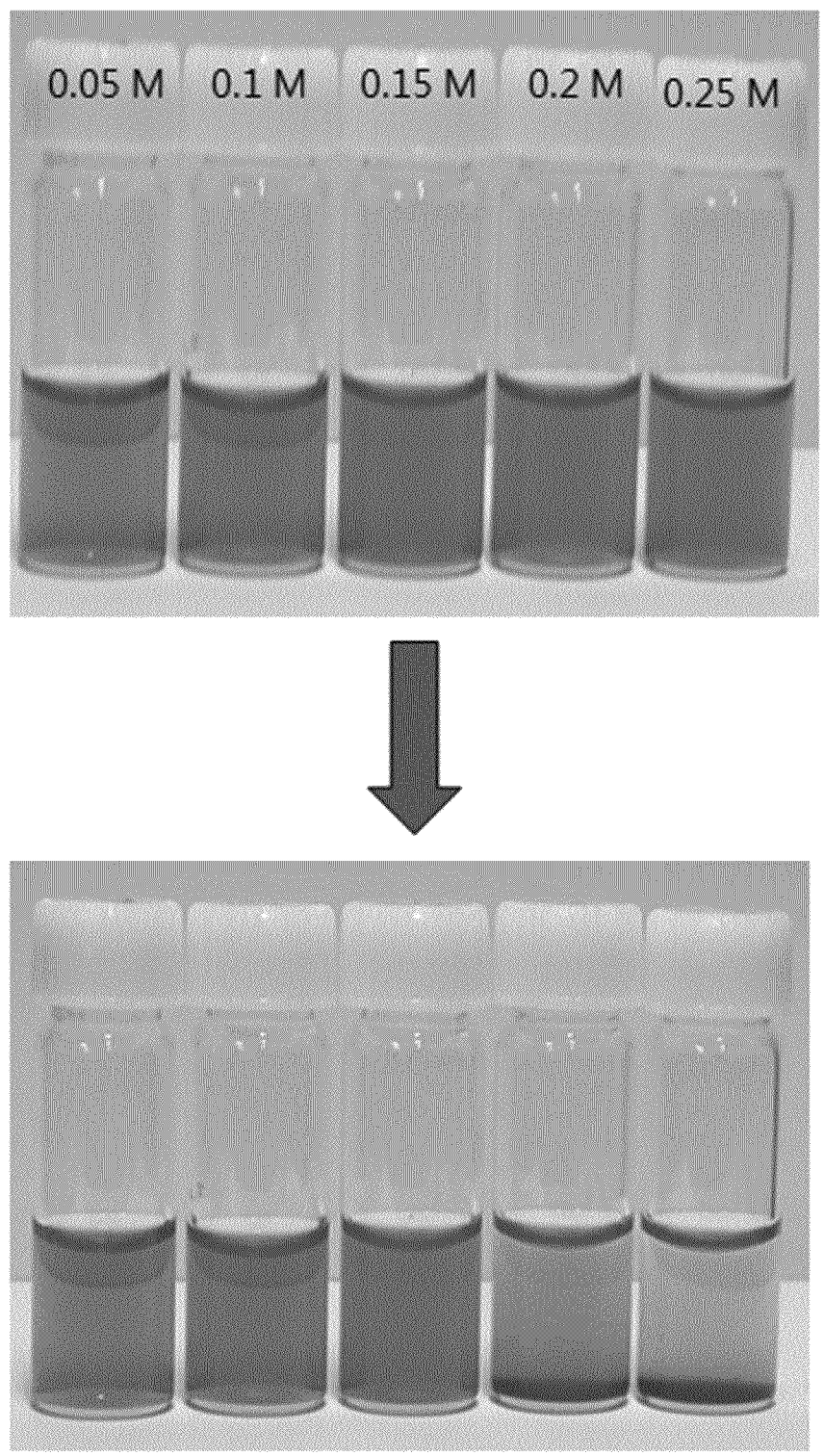
FIG. 12 shows photographs of samples of the CM-dextran-coated iron oxide nanoparticles with respect to changes in NaCl concentration.

In order to validate the colloidal stability of the iron oxide nanoparticles coated with hydrophilic material, changes in diameter of the iron oxide nanoparticles upon changes in pH and upon heating were observed. The DS-coated iron oxide nanoparticles were stable in the pH range of 4 to 11 (FIG. 9). Also, the DS-coated iron oxide nanoparticles had no size change at 100° C. for 4 hr. However, the DS-coated iron oxide nanoparticles were unstable in the NaCl solution and thus observed to sink. The CM-dextran-coated iron oxide nanoparticles were stable in the pH range of 4 to 13, but the nanoparticles became unstable at pH 3 and were observed to rapidly sink (FIGS. 10 and 11). Measuring the zeta potential showed that the nanoparticles which had been stable had a value of −23.74~−36.88 mV but the potential value was 1.81 mV at pH 3 (FIG. 11). These results show that about pH 3 is regarded as an isoelectric point and the zeta potential is lowered whereby the nanoparticles become unstable. Thus, the electrostatic action (repulsive force) is seen to contribute to the stability of the nanoparticles. The CM-dextran-coated iron oxide nanoparticles also had no size change at 100° C. for 4 hr. Such nanoparticles were stable up to the NaCl concentration of 0.15 M (FIGS. 10 and 12). Thereby, the stability of the CM-dextran-coated nanoparticles can be seen to be suitable for medical applications. The DS-coated nanoparticles are unstable in the NaCl solution and thus are not suitable for medical applications.

Figure 13:
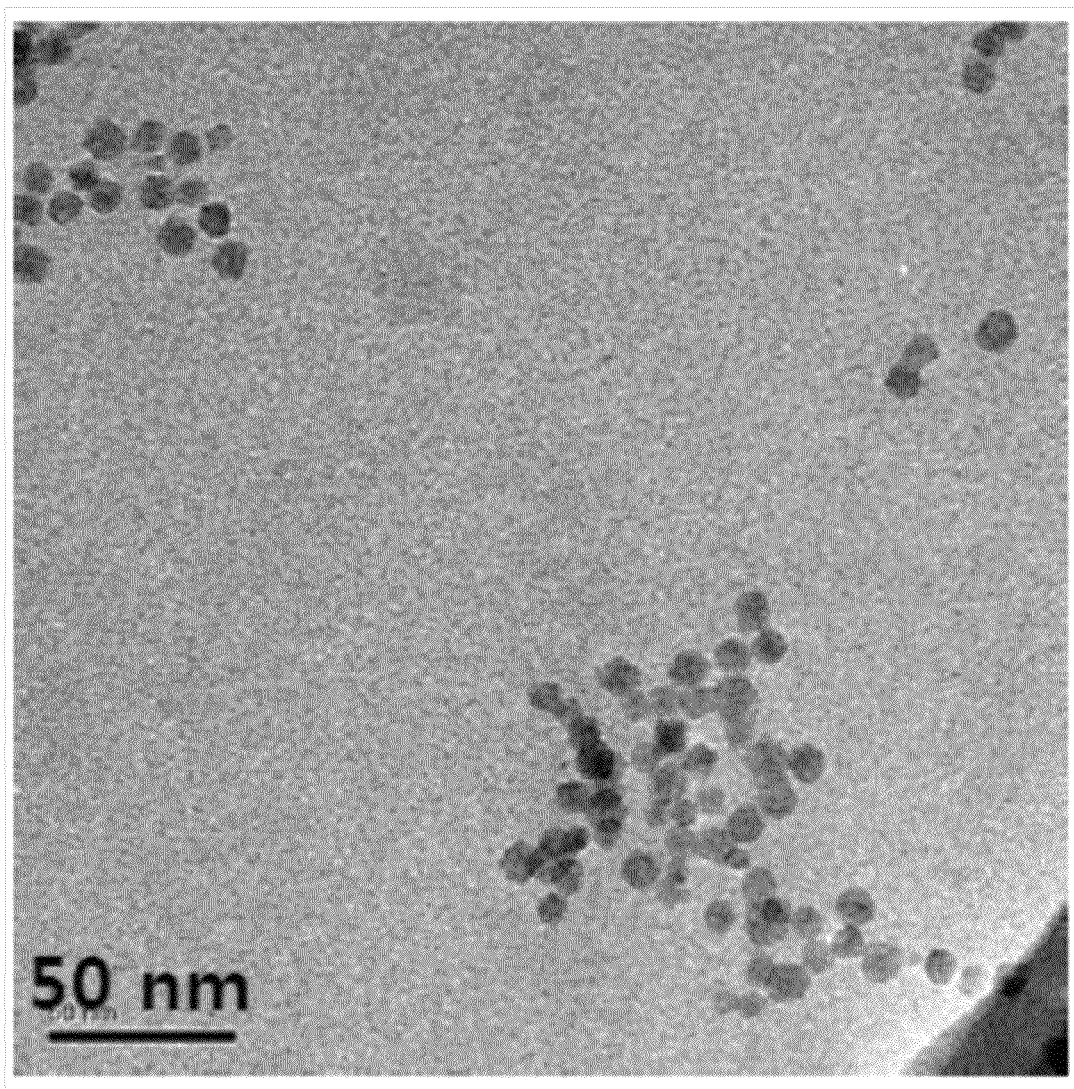
FIG. 13 shows a TEM image of polyacrylic acid-coated iron oxide nanoparticles.

Because a polyacrylic acid (Mw 1,800) solution is acidic, the iron oxide nanoparticles coated with polyacrylic acid have low dispersibility in an aqueous solution immediately after removal of the salt. As the pH is increased by the addition of sodium hydroxide (NaOH), dispersibility is improved and the hydrodynamic diameter is decreased (Table 4). This is because the carboxylic acid that forms the polyacrylic acid is negatively charged under basic conditions. The hydrodynamic diameter was 91.9 nm under acidic conditions, 59.4 nm under neutral conditions and 39.9 nm under basic conditions. As shown in the TEM image, the particles did not agglomerate while being coated with polyacrylic acid (FIG. 13).

Figure 14:
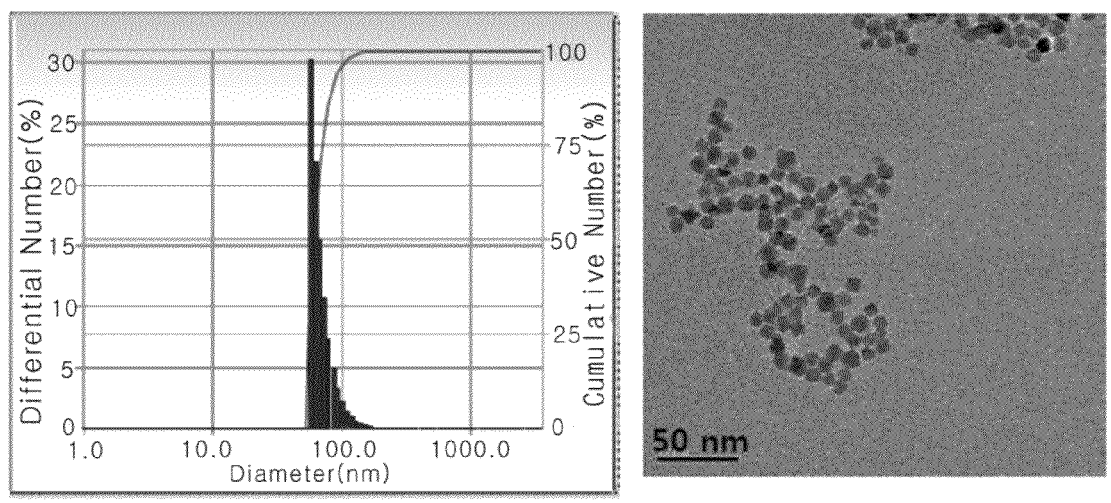
FIG. 14 shows a TEM image of PEG-phosphate (PO-PEGs)-coated iron oxide nanoparticles and a graph showing the hydrodynamic diameter thereof.

The PEG-phosphate (PO-PEGs)-coated iron oxide nanoparticles were well dispersed in an aqueous solution. As shown in the TEM image, the particles did not agglomerate while being coated with PO-PEGs and had a hydrodynamic diameter of 69.2 nm (FIG. 14).

Example 3

Preparation of DS-Coated Iron Oxide Nanoparticles Via Annealing Treatment Using Small Salt Particles DS-coated iron oxide nanoparticles were prepared in the same manner as in Example 2 with the exception that the size of salt particles was 13 μm. The hydrodynamic diameter of the DS-coated iron oxide nanoparticles was 31.03 nm (Table 3).

TABLE 3

| | Hydrophilic Material | Hydrodynamic Diameter (nm) |
|---|---|---|
| Ex. 2 | DEAE-dextran | 84.3 |
| Ex. 2 | DS | 36.8 |
| Ex. 2 | Dextran | 157.0 |
| Ex. 2 | CM-dextran | 66.4 |
| Ex. 2 | PEG-phospholipid | 28.7 |
| Ex. 3 | DS (salt particle size: 13 μm) | 31.03 |

TABLE 4

| pH | Hydrodynamic Diameter (nm) |
|---|---|
| 2 | 91.9 |
| 8 | 59.4 |
| 12 | 39.9 |

Example 4

Cell Toxicity Test of Iron Oxide Nanoparticles Coated with Dextran Derivative

Figure 15:
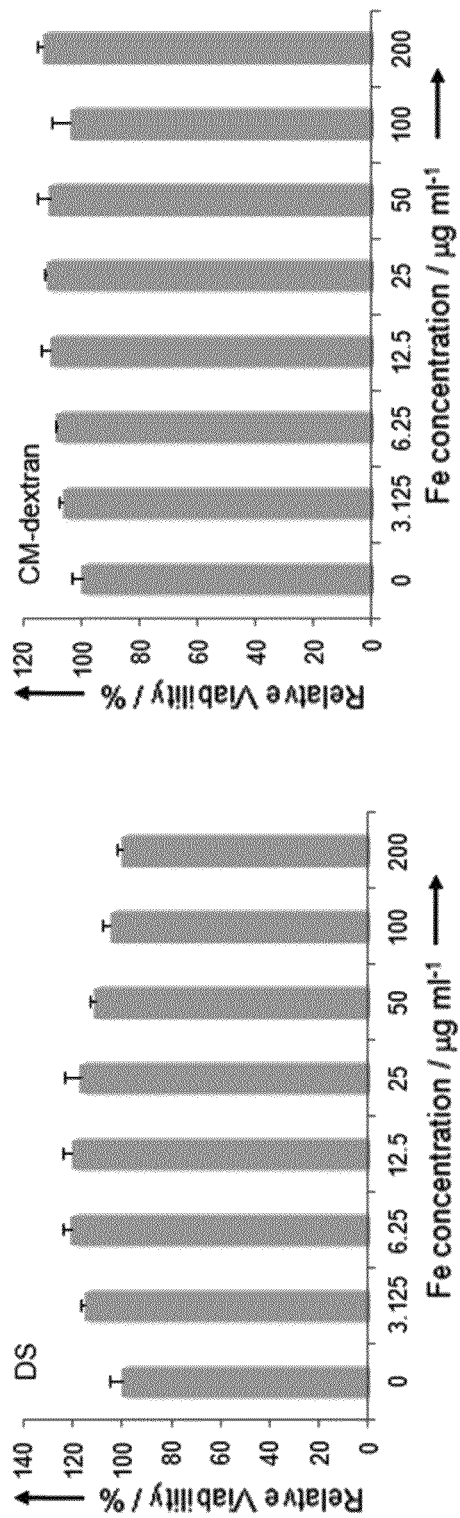
FIG. 15 is of graphs showing the cell toxicity test results of the DS-coated iron oxide nanoparticles and the CM-dextran-coated iron oxide nanoparticles.

The DS-coated and the CM-dextran-coated iron oxide nanoparticles were measured using MTT method. The iron oxide nanoparticles at different concentrations were cultured in cells for 48 hr, after which the survival rate of cells was measured. Consequently, almost all of the cells were alive up to the concentration of 200 μg [Fe]/ml (FIG. 15).

Example 5

Figure 16:
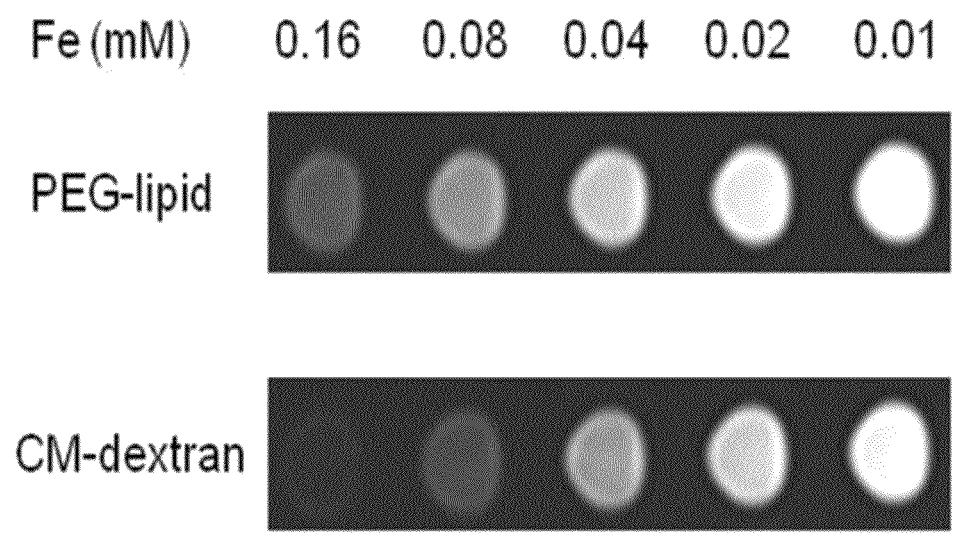
FIG. 16 shows MRI results using the CM-dextran-coated iron oxide nanoparticles.
Figure 17:
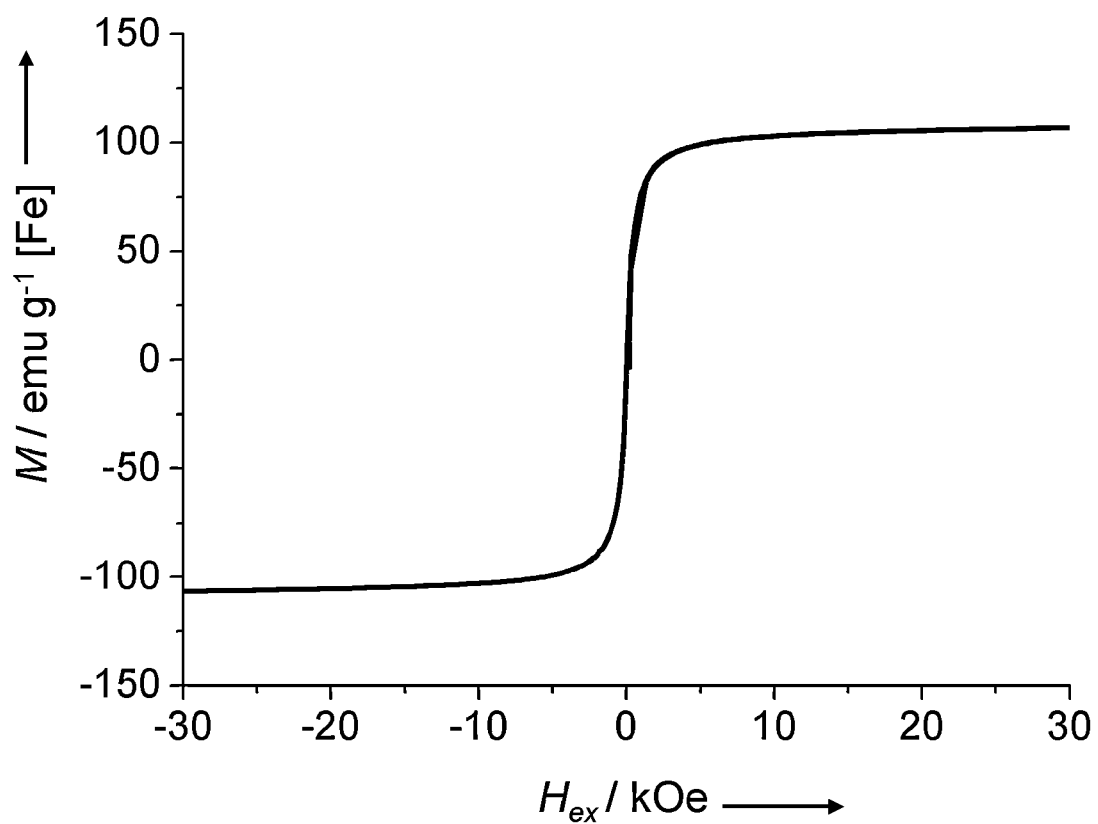
FIG. 17 is a graph showing the magnetic data of the CM-dextran-coated iron oxide nanoparticles.

Applicability Test of Iron Oxide Nanoparticles Coated with Dextran Derivative as MRI Contrast Agent The iron oxide nanoparticles were coated using CM-dextran instead of DS because of superior stability. The T2 MRI image of the nanoparticles dispersed in the aqueous solution shows a decrease in signal in proportion to an increase in the concentration of iron ions (FIG. 16). To evaluate the contrast effects, r2 relaxivity was calculated, which is a gradient of a reciprocal of T2 relaxation time relative to a concentration of the contrast agent. This is an indicator that shows how much the T2 relaxation time sensitively varies depending on changes in concentration of the contrast agent. The r2 relaxivity was calculated from $1/T2=1/T2_0+r2*C$ wherein T2 is the T2 relaxation time, $T2_0$ is the initial T2 relaxation time, and C is the concentration of the contrast agent. In the graph plot wherein the concentration of the contrast agent including the iron oxide nanoparticles coated with hydrophilic material is set to the x-axis and the 1/T2 measured at the above concentration is set to the y-axis, r2 is derived from the gradient, wherein r2 designates the r2 relaxivity. The relaxivity of the iron oxide nanoparticles coated with PEG-phospholipid without annealing treatment was 124.46 $mM^{-1}s^{-1}$ and that of the iron oxide nanoparticles coated with CM-dextran after annealing treatment was 358.9 $mM^{-1}s^{-1}$ which is an increase of 2.9 times. Such a high relaxivity is based on increased crystallinity during annealing treatment and coating of a plurality of particles with a single dextran shell in the course of coating with CM-dextran. As described in Example 1, the saturation magnetization after annealing treatment was increased because of additional crystallization. Even after coating with CM-dextran, the saturation magnetization (106 emu/g [Fe]) was similar to that after annealing treatment (FIG. 17). When the dispersed superparamagnetic nanoparticles agglomerated, the increase in r2 relaxivity was reported to be based on the magnetic relaxation switch (J. M. Perez, et. al. Chem. Bio. Chem. 2004, 5, 261). When a material having high contrast effect is used in this way, the amount of introduced nanoparticles in vivo may be decreased, thus lowering the toxic effects. Hence, the CM-dextran-coated iron oxide nanoparticles are determined to be useful as a biocompatible MRI contrast agent having high contrast effects.

Figure 18:
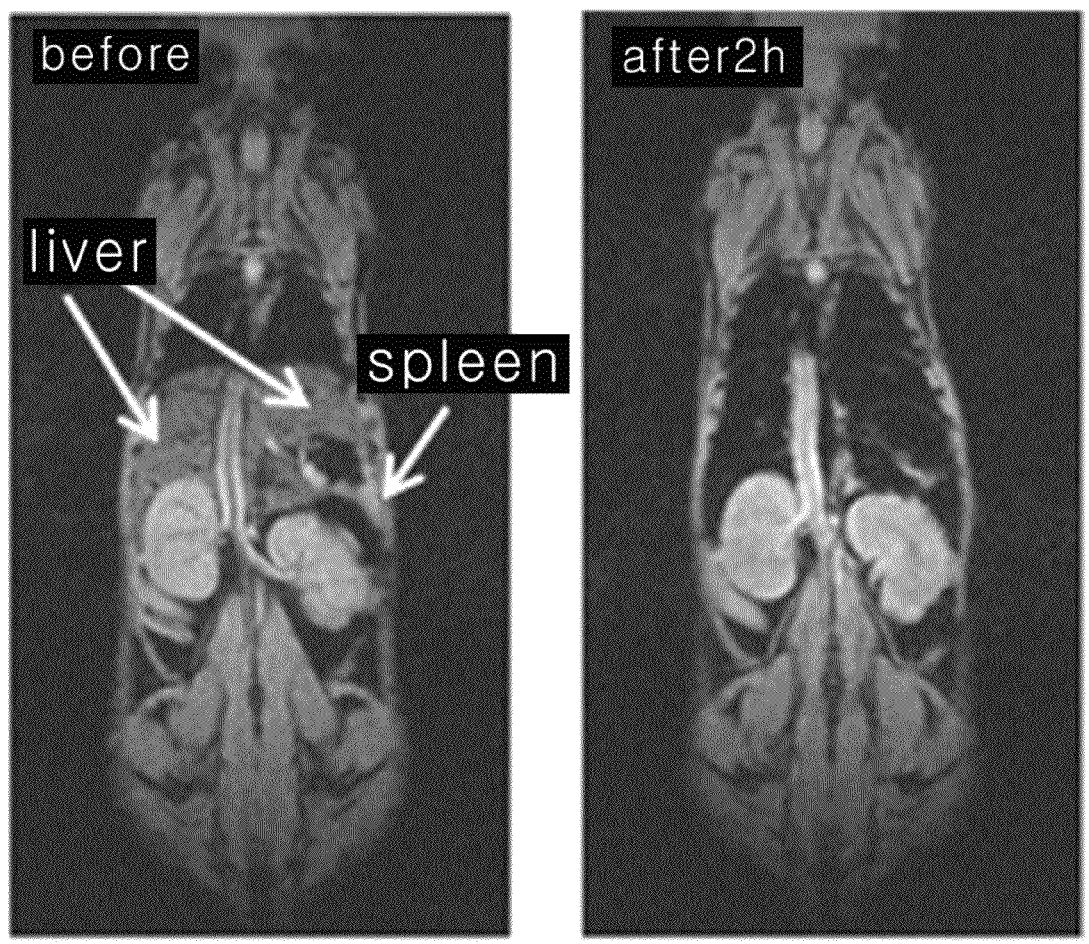
FIG. 18 shows MRI results of animal testing using the CM-dextran-coated iron oxide nanoparticles.

The CM-dextran-coated iron oxide nanoparticles were applied to animal MRI testing. The nanoparticles (2.5 mg [Fe] per kg of mouse body weight) were injected via the tail vein of the mouse. The MRI results before and after the injection of the nanoparticles show that the nanoparticles accumulate in the liver and the spleen thus achieving effective contrast (FIG. 18). These nanoparticles were confirmed to be suitable for application in vivo.

The invention claimed is:

1. A method of preparing iron oxide nanoparticles coated with a hydrophilic material, comprising:
    a) annealing a power mixture comprising salt particles and magnetic iron oxide nanoparticles coated with a hydrophobic organic material, thus obtaining iron oxide nanoparticles having no organic material; and
    b) coating a surface of the iron oxide nanoparticles having no organic material with a hydrophilic material,
    wherein the annealing in a) is performed under air conditions.

2. The method of claim 1, wherein the hydrophobic organic material coated to the iron oxide nanoparticles in a) is at least one selected from the group consisting of a $C_4$~$C_{25}$ fatty acid, a $C_4$~$C_{25}$ aliphatic alcohol, and a $C_4$~$C_{25}$ aliphatic amine.

3. The method of claim 2, wherein the fatty acid is oleic acid.

4. The method of claim 1, wherein the salt particles in a) is at least one selected from the group consisting of sodium sulfate ($Na_2SO_4$), sodium bicarbonate ($NaHCO_3$), potassium bicarbonate ($KHCO_3$), calcium bicarbonate ($Ca(HCO_3)_2$), sodium chloride (NaCl), potassium chloride (KCl) and calcium chloride ($CaCl_2$).

5. The method of claim 1, wherein the salt particles in a) have a diameter of 1~500 μm.

6. The method of claim 1, wherein the magnetic iron oxide nanoparticles in a) are obtained by reacting an iron complex comprising iron as a center atom and a $C_4$~$C_{25}$ organic acid group (carboxylate) attached thereto as a ligand with a $C_4$~$C_{25}$ fatty acid.

7. The method of claim 6, wherein the iron complex is iron oleate.

8. The method of claim 6, wherein the fatty acid is oleic acid.

9. The method of claim 1, wherein the magnetic iron oxide nanoparticles in a) have a diameter of 1~100 nm.

10. The method of claim 1, wherein the magnetic iron oxide nanoparticles and the salt particles in a) have a weight ratio ranging from 1:10 to 1:1000.

11. The method of claim 1, wherein the annealing in a) is performed by carrying out heating at 400~600° C. for 1~10 hr in an air atmosphere.

12. The method of claim 1, wherein, after annealing in a), removing the salt particles is additionally performed.

13. The method of claim 12, wherein the removing the salt is performed using centrifugation.

14. The method of claim 12, wherein the temperature is decreased to room temperature before the removing the salt after annealing in a).

15. The method of claim 1, wherein the hydrophilic material in b) is a dextran derivative, polyacrylic acid, starch, silica, polyethyleneglycol (PEG) or PEG-phosphate (PO-PEGs).

16. The method of claim 15, wherein the dextran derivative is diethylaminoethyl-dextran (DEAE-dextran), dextran sulfate (DS) or carboxymethyl dextran (CM-dextran).

17. The method of claim 1, wherein removing the salt are simultaneously performed with the coating in b).

* * * * *